United States Patent [19]
Pagay et al.

[11] Patent Number: 5,411,489
[45] Date of Patent: May 2, 1995

[54] PRE-FILLED SYRINGE AND PRE-FILLED CARTRIDGE HAVING ACTUATING CYLINDER/PLUNGER ROD COMBINATION FOR REDUCING SYRINGING FORCE

[75] Inventors: Shrikant N. Pagay, Guilderland, N.Y.; Robert J. Bachorik, II, Phoenixville, Pa.; Richard T. Liebert, Milton, N.Y.

[73] Assignee: Sterling Winthrop Inc., New York, N.Y.

[21] Appl. No.: 239,095

[22] Filed: May 6, 1994

[51] Int. Cl.⁶ .................................... A61M 5/00
[52] U.S. Cl. .......................... 604/218; 604/220; 604/228
[58] Field of Search ............... 604/218, 220, 221, 228, 604/230, 232, 110, 187

[56] References Cited

U.S. PATENT DOCUMENTS

| | | |
|---|---|---|
| Re. 32,974 | 7/1989 | Porat et al. |
| 1,222,424 | 4/1917 | Laurent. |
| 1,707,880 | 4/1929 | Sheets. |
| 3,669,111 | 6/1972 | Dubner. |
| 3,705,582 | 12/1972 | Stumpf et al. |
| 3,766,918 | 10/1973 | Kessel. |
| 3,834,387 | 9/1974 | Brown. |
| 4,216,771 | 8/1980 | Arlers et al. |
| 4,299,238 | 11/1981 | Baidwan et al. |
| 4,333,457 | 6/1982 | Margulies. |
| 4,543,093 | 9/1985 | Christinger ............... 604/228 |
| 4,562,844 | 1/1986 | Carpenter et al. ........ 604/220 X |
| 5,259,840 | 11/1993 | Boris ........................ 604/218 X |
| 5,263,934 | 11/1993 | Haak ........................ 604/110 |

*Primary Examiner*—John D. Yasko
*Attorney, Agent, or Firm*—Fish & Richardson

[57] ABSTRACT

Disclosed are pre-filled syringes equipped with an improved plunger, a plunger actuating cylinder and a plunger rod, characterized by a leak-proof seal and easy sliding property.

16 Claims, 5 Drawing Sheets

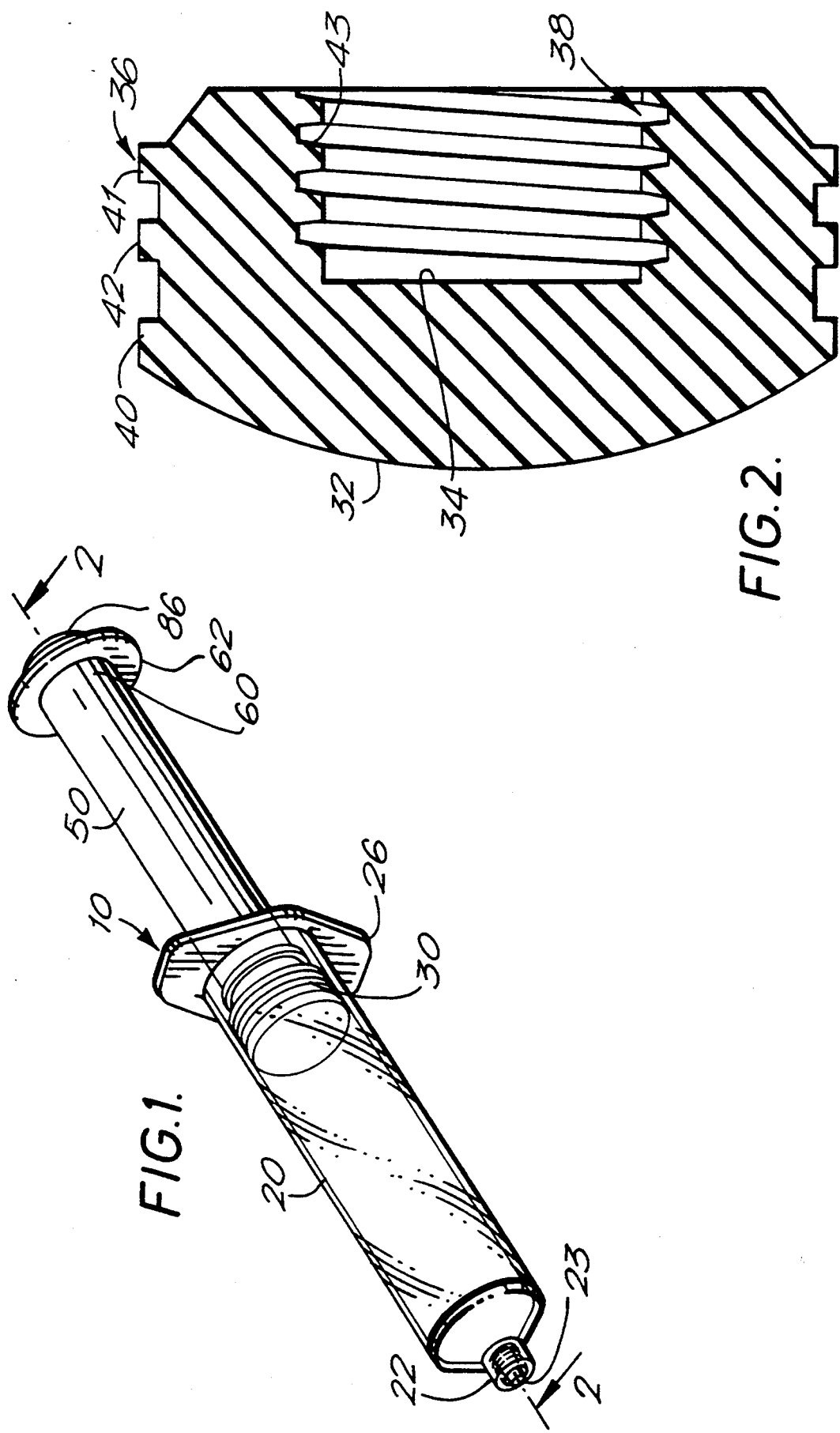

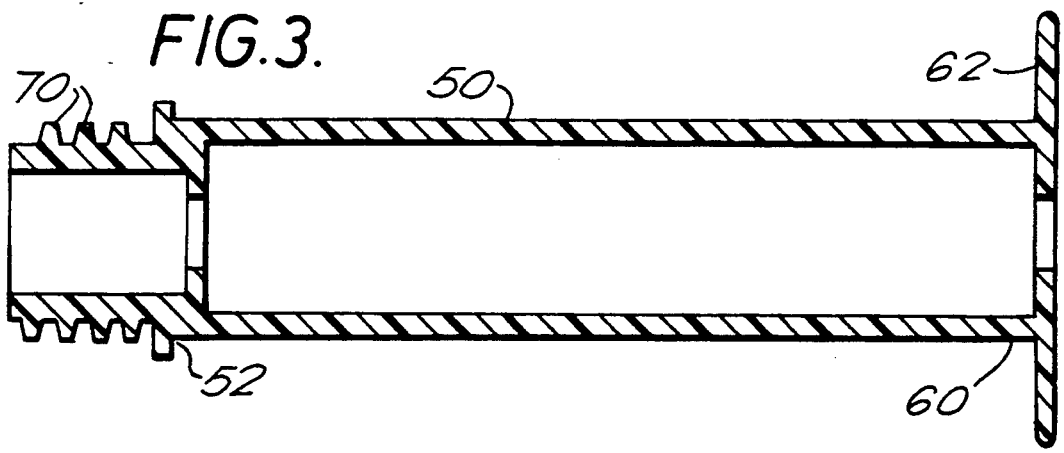
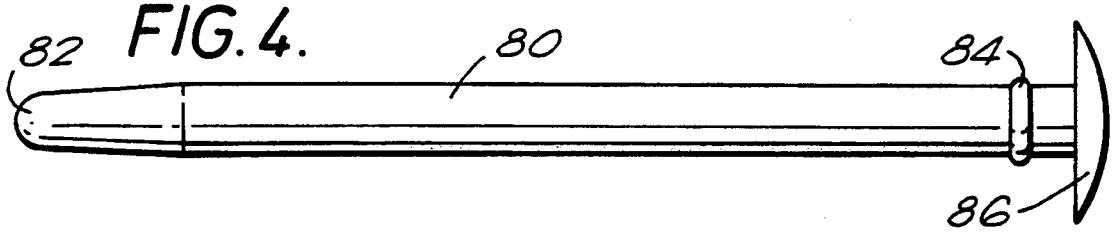
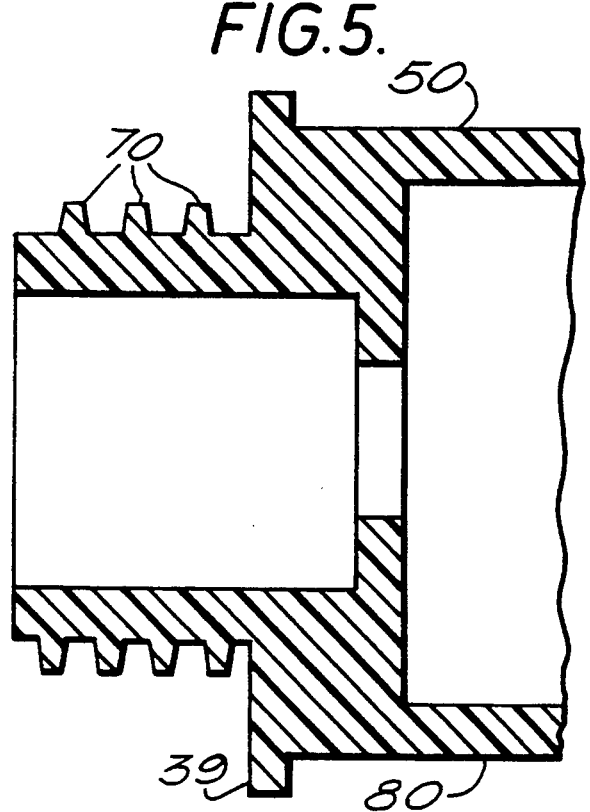

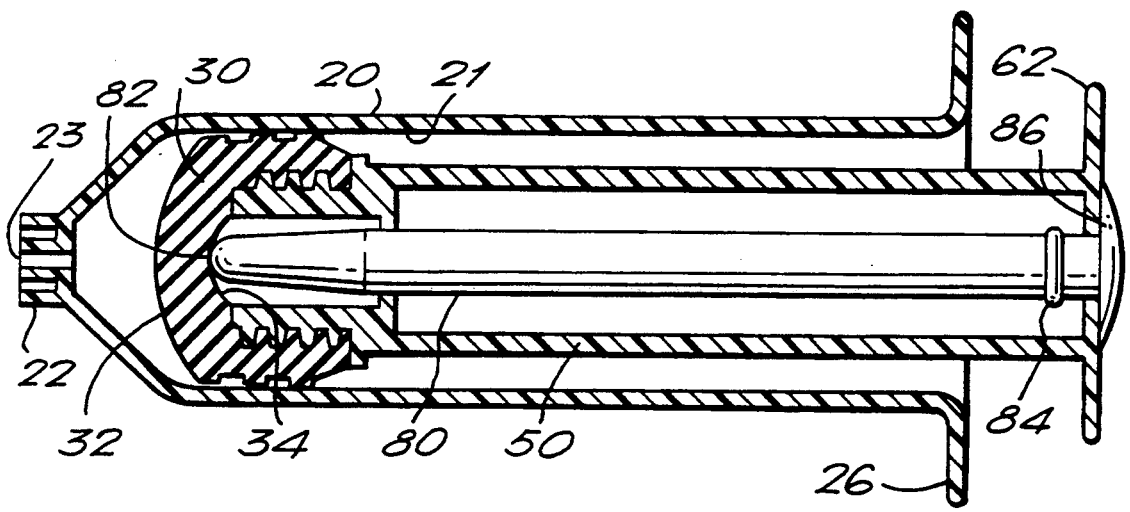
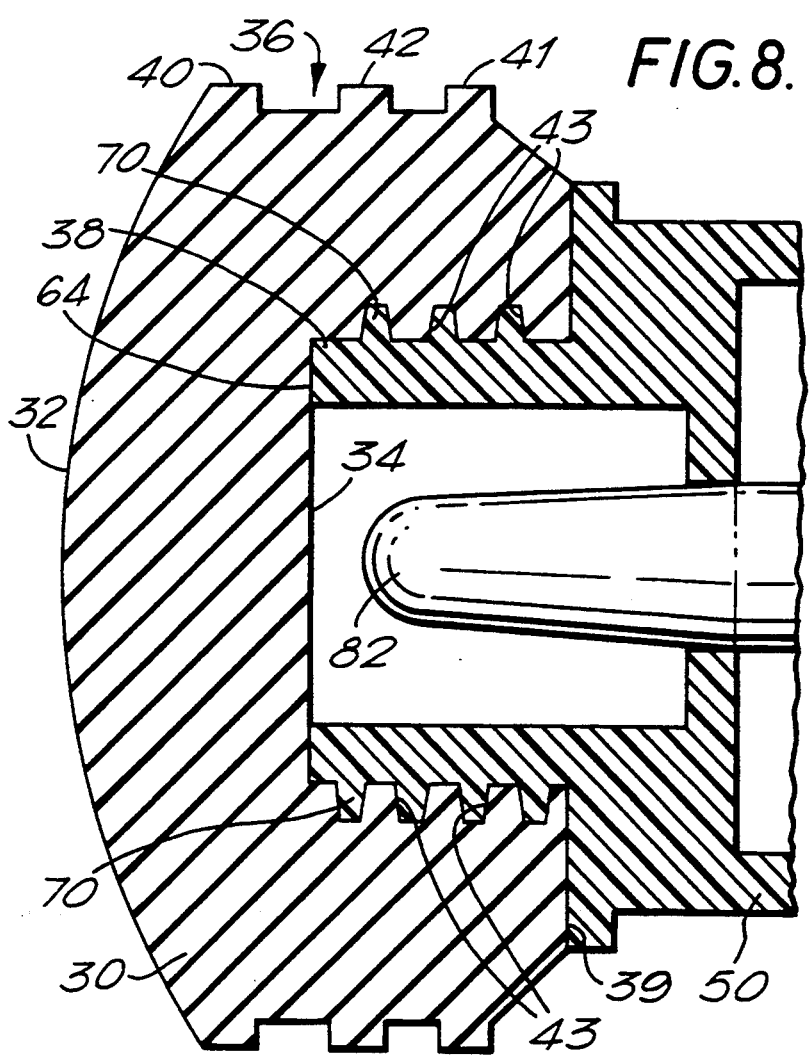

PRE-FILLED SYRINGE AND PRE-FILLED CARTRIDGE HAVING ACTUATING CYLINDER/PLUNGER ROD COMBINATION FOR REDUCING SYRINGING FORCE

BACKGROUND OF THE INVENTION

1. Field of the Invention

This invention relates generally to pre-filled syringes and pre-filled cartridges for administering various fluids into a patient, more particularly, the invention relates to plastic syringes and cartridges for injecting liquid pharmaceutical/biological agents, such as diagnostic imaging agents into a patient.

2. Reported Developments

Various syringes for taking body fluid samples or administering fluid medicaments to a patient are known. Such syringes generally include a cylindrical syringe barrel, a hypodermic needle engaged with the syringe barrel, and a plunger within the syringe barrel which, when a force is exerted axially by an operator, create a suction force drawing body fluids into the barrel, or delivers fluid medicament through the hypodermic needle. The purpose of the plunger is to provide an air tight seal between itself and the syringe barrel so that movement of the plunger up and down the barrel will allow liquid, blood or other fluids to be drawn into or forced out of the syringe through the distal end.

Syringes used for such purposes include glass syringes, in which the cylindrical barrel is made of glass and the plunger is a ground glass rod which closely fits within the cylindrical barrel. In order to eliminate leakage and at the same time reduce resistance to an acceptable level, close tolerances are necessary between the barrel and the plunger along with the use of a lubricant. These glass syringes suffer from a number of disadvantages including that: they are expensive since they require close tolerances; they cannot be easily mass produced since the plungers often cannot be interchanged with one another and have to be individually fit with the barrel during the grinding process by the manufacturer; and they are susceptible to breakage.

To obviate these problems syringes were proposed and/or made by using glass and plastic barrels with plastic or elastomeric plungers. In order to prevent leakage around the plunger, the plunger is made with one or more ribs which are slightly larger in diameter in the uncompressed state than the inside of the barrel which upon placement within the barrel are compressed and deformed against the wall of the barrel and thereby form a seal. The quality and strength of the seal depend on the elastomeric properties of the material used to make the plunger and the ratio of the respective diameters of the plunger and the inside of the barrel. To obtain a good leak-proof seal, a relatively large compressive force must be exerted on the elastomeric plunger by the syringe barrel. This quality of seal, however, makes the movement of the plunger within the barrel difficult requiring excessive force on the part of the operator to move the plunger. This drawback is even more pronounced with pre-filled syringes which are maintained, ready to use, in storage. During this shelf-life the plunger tends to bind with the barrel. To remedy the problem the prior art used lubricants to reduce friction and drag between the plunger and the inside of the syringe barrel. One of the commonly used lubricants for this purpose is silicone oil. The use of such lubricants is, however, undesirable, since the lubricants tend to disperse and/or dissolve in parenteral formulations thereby contaminating the formulations. Such potential adulteration is, of course, undesirable and attempts were made to avoid the use of lubricants and still provide a leakage-proof syringe with easily slideable plunger. Such attempts included the use of various plunger configurations including one or more ribs thereon projecting forwardly or rearwardly in the barrel to reduce the frictional drag between the plunger and the barrel. Another approach was, for example in U.S. Pat. No. 5,009,646, to laminate the elastomeric plunger with a film of tetrafluoroethylene, ethylenetetrafiuoroethylene or ultrahigh molecular weight polyethylene resin.

While liquid tightness and sliding property have somewhat improved with these attempts as regards to syringes intended for taking body fluid samples or injecting medicaments from stored vials, the problem of inadequate sliding property in pre-filled syringes stored for extended time periods still remain unsolved.

It is a main object of the present invention to provide a pre-filled syringe and a pre-filled cartridge which will overcome the above-described inadequate sliding property while maintaining a tight, leak-proof seal between the plunger and the wall of the syringe barrel.

It is another object of the present invention to provide a self-aspirating syringe and cartridge.

In medical practice, hypodermic injections are sometimes administered subcutaneously, while others must be given intravenously, depending upon the particular medication to be administered. In either case, it is essential that the practitioner know with certainty, prior to injection of the medication whether the hypodermic needle tip is located in a major blood vessel, such as a vein, or in subcutaneous tissue. Use of an aspirating syringe in which a negative pressure can be generated in the syringe affords a means of making such determination. Thus the appearance of blood in the syringe upon generation of the negative pressure would indicate location of the needle tip in a major blood vessel, while the lack of appearance of blood would indicate location of the tip in subcutaneous tissue. Depending upon the type of injection intended, the injection can then either proceed directly or if appropriate, the tip can be withdrawn and relocated.

Aspirating syringes are generally of two types, namely, they are either manually or automatically aspirated. In the manually aspirated type the plunger is retracted for a short distance within the barrel of the syringe. This retraction lowers the pressure within the syringe which leaves fluids at the needle tip which are then observable within the barrel of the syringe. From solid tissues no fluids will be drawn into the barrel. In the manually aspirated syringes the injection necessitates the use of both hands, one to hold the barrel, and the other to exert pressure in a rearward direction on the plunger. Such manually actuatable aspirating syringes have the disadvantage that their proper use depends on very large measure on the degree of skill of the person administering the injections.

Aspiration in syringes of the automatic or self-aspirating type is effected by first inducing a positive pressure in a medicament-containing portion of the syringe. On release of the force inducing the positive pressure, a corresponding negative pressure in the syringe is generated thus giving rise to the aspirating effect. The present invention relates to the self-aspirating type syringes.

Ideally a self-aspirating hypodermic syringe should be: relatively simple in construction so as to minimize the cost of production; relatively simple to operate; capable of manipulation with one hand; adaptable to multiple self-aspirating actions; capable of expelling trapped air from the syringe prior to insertion of the needle into the injection site and prior to initiation of the self-aspirating action without either precluding self-aspirating action at a later time in the operation sequence of the syringe or otherwise rendering it inoperative.

The self-aspirating syringes provided by the present invention mimic, automatically, the slight rearward piston displacement withdrawal action of manually operable syringes, thus generating the slight negative pressure in the syringes essential for aspiration. The syringes of the present invention therefore obviate the disadvantage inherent in prior art syringes of the manual type, since the aspirating action is generated automatically which requires no special skill on the part of the practitioner.

These and other desirable objects will be explained as the description proceeds.

The invention will be described in reference to a pre-filled syringe; however, it is to be understood that a pre-filled cartridge, having essentially the same shape and other characteristics as a pre-filled syringe, is also intended to be described and covered by the appended claims.

SUMMARY OF THE INVENTION

The present invention comprises a syringe which is designed to be pre-filled and stored ready for injection. The syringe comprises:

(a) a barrel having an inner surface defining a cylindrical chamber for retaining an injectable fluid therein; a distal end terminating in a tapered tip to which an injection needle can be attached; and a proximal end for receiving a plunger;

(b) a cup-shaped plunger slideably mounted in said barrel and positioned close to the proximal end of the barrel to provide a seal with the inner surface of the barrel, said plunger comprising:
 (1) a distal convex face which is to interface with the injectable fluid contained in the barrel;
 (2) a proximal face;
 (3) outside wall contiguous with the distal convex face having thereon: distal ring, proximal ring and center ring extending radially outwardly and forming a slideable seal with the inner surface of the barrel;
 (4) inside wall having female threads;
 (5) bottom rim which together with the inside wall defines a circular opening in the cup-shaped plunger through which a plunger actuating cylinder is inserted for engagement;

(c) a plunger actuating cylinder having a distal end and proximal end for engaging the plunger comprising:
 (1) male threads at the distal end to engage female threads in the plunger; and
 (2) a handle at the proximal end; and (d) a plunger rod, having a distal end and a proximal end, fitted into said plunger actuating cylinder comprising:
 (1) a semi-circular shaped tip at the distal end with convex face projecting in the direction of the plunger and the diameter of which is substantially smaller than the diameter of the plunger to press against the proximal face of the plunger when pressure is being exerted on the plunger rod;

(2) a knob at the proximal end located outside the plunger actuating cylinder and serving as first stopping means for the plunger rod to limit protrusion of the plunger rod into the proximal face of the plunger; and (3) a flange also at the proximal end but spaced from the knob and located within the plunger actuating cylinder and serving as second stopping means for the plunger rod to limit the movement of the plunger rod in the direction toward the proximal end of the plunger actuating cylinder;

said first stopping means and second stopping means are designed to limit the movement of the plunger rod within the plunger actuating cylinder to a predetermined length defined by the distance between the first and second stopping means.

BRIEF DESCRIPTION OF THE DRAWINGS

FIG. 1 is a perspective view of the assembled syringe comprising a syringe barrel, a plunger, a plunger actuating cylinder and a plunger rod according to the present invention;

FIG. 2 is a longitudinal cross-section of the plunger taken along the line 2—2 of FIG. 1;

FIG. 3 is a longitudinal cross-section of the plunger actuating cylinder taken along the line 2—2 of FIG. 1;

FIG. 4 is a longitudinal cross-section of the plunger rod taken along the line 2—2 of FIG. 1;

FIG. 5 is an enlarged fragmentary cross-section of the plunger actuating cylinder;

FIG. 7 is a longitudinal cross-section of the assembled syringe comprising the syringe barrel, the plunger, the plunger actuating cylinder and the plunger rod taken along the line 2—2 of FIG. 1 when the plunger rod is in its extended position;

FIG. 8 is an enlarged fragmentary cross-section of the plunger, the plunger actuating cylinder and the plunger rod when plunger rod is in its base position.

Figure 6:
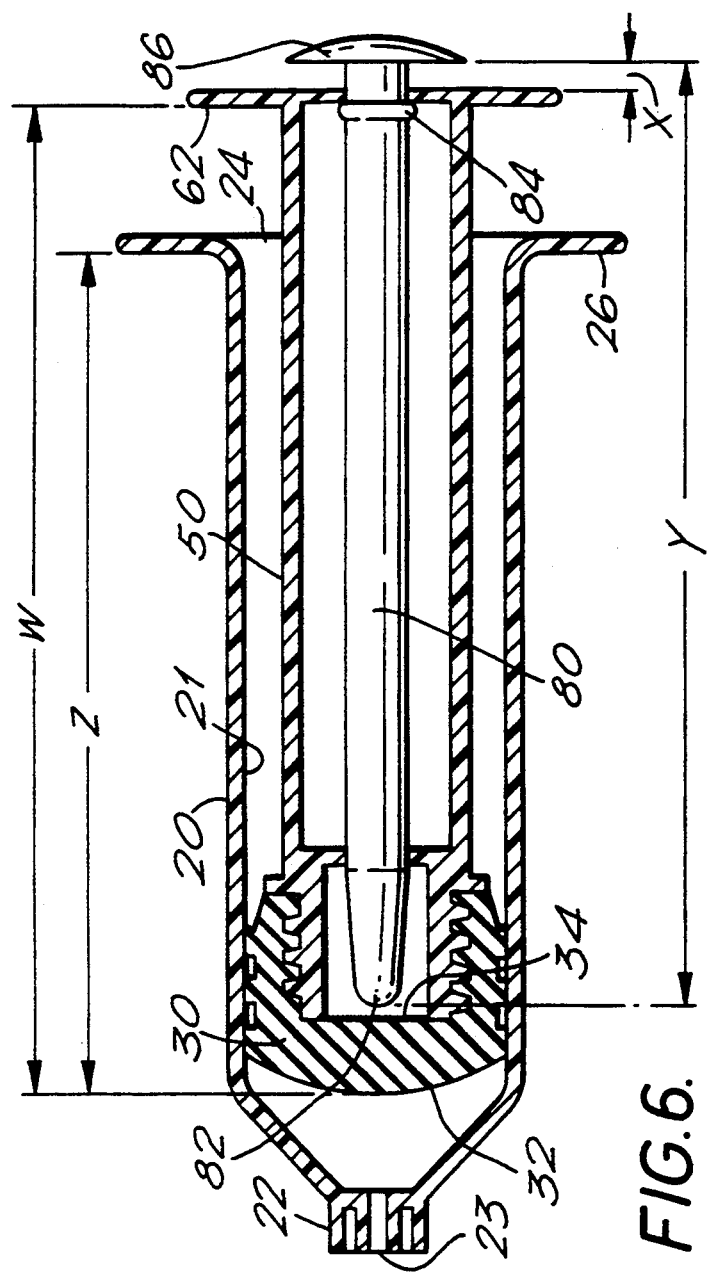
FIG. 6 is a longitudinal cross-section of the assembled syringe comprising the syringe barrel, the plunger, the plunger actuating cylinder and the plunger rod taken along the line 2—2 of FIG. 1 when the plunger rod is in a base position.

| LIST OF REFERENCE NUMBERS USED | |
|---|---|
| Syringe (generally designated) | 10 |
| Syringe barrel | 20 |
| Inside wall of barrel | 21 |
| Plunger | 30 |
| Plunger actuating cylinder | 50 |
| Tapered tip of barrel at distal end | 22 |
| Bore through tip of barrel | 23 |
| Proximal end of barrel | 24 |
| Finger hub of barrel | 26 |
| Distal end of plunger actuating cylinder | 52 |
| Proximal end of plunger actuating cylinder | 60 |
| Handle of plunger actuating cylinder | 62 |
| Convex outside face of plunger | 32 |
| Inside face of plunger | 34 |

-continued

LIST OF REFERENCE NUMBERS USED

| | |
|---|---|
| Outside wall of plunger | 36 |
| Inside wall of plunger | 38 |
| Bottom rim of plunger | 39 |
| Distal ring (on outside wall of plunger) | 40 |
| Proximal ring (on outside wall of plunger) | 41 |
| Center ring (on outside wall of plunger) | 42 |
| Female threads (of plunger on inside wall) | 43 |
| Male thread (on plunger actuating cylinder) | 70 |
| Plunger rod | 80 |
| Tip of plunger rod | 82 |
| Flange (on plunger rod) | 84 |
| Knob (on plunger rod) | 86 |
| Protrusion length (of plunger rod) | X |
| Total length of plunger rod | Y |
| Total length of plunger actuating cylinder plus plunger | W |
| Total length of functional (working) portion of syringe barrel | Z |

DESCRIPTION OF THE PREFERRED EMBODIMENTS

Referring to FIGS. 1, 2, 3, 4 and 6 there is shown a syringe generally designated 10 comprising:

syringe barrel 20 having inside wall 21, distal end terminating in a tapered tip 22 which has a bore 23 therethrough, and proximal end 24 terminating in finger hub 26;

plunger 30 slideably positioned in barrel 20;

plunger actuating cylinder 50 having distal end 52 and proximal end 60, comprising male threads 70 located on the distal end, and handle 62 located on the proximal end thereof, and is designed to engage plunger 30 in barrel 20; and plunger rod 80 comprises semi-circular plunger rod tip 82 at its distal end, flange 84, and knob 86 at its proximal end, said plunger rod is to be received by said plunger actuating cylinder 50.

Syringe barrel 20 is made of an inert gas impermeable material including glass, however, it is preferably made of a substantially transparent material that is somewhat more flexible than glass, such as polyethylene, polypropylene, polystyrenes, acrylic and methacrylic polymers.

Plunger 30 is made of a compressible, elastomeric material, such as polyisoprene rubber. Plunger actuating cylinder is made of hard plastic material including polyethylene, polypropylene, polystyrenes, acrylic and methacrylic polymers. Plunger rod 80 is made essentially of the same material as the barrel.

Referring to FIGS. 2, 5, 6 and 7, plunger 30 is slideably positioned in syringe barrel 20 at its proximal end 24 thereof. When plunger 30 is at this position, syringe barrel is placed pointing vertically upward with its distal end on a flat surface, such as filling line, without interference from plunger 30. Syringe barrel 20 is then filled with the desired liquid, such as a medicament or a diagnostic imaging medium through bore 23 in tapered tip 22 and capped. The liquid introduced into the syringe barrel can be pre-sterilized in bulk and filled into the syringe barrel using aseptic technique or the pre-filled syringe may be sterilized by autoclaving or by other means at this point. After the filling process is completed and the syringe is capped, the syringe is packaged to be stored without the syringe actuating cylinder 50 and plunger rod 80 being engaged with the syringe barrel.

An alternate filling procedure is to cap tapered tip 22 and fill the medication from the proximal end of barrel 20. Plunger 30 is then inserted in to barrel 20 after filling syringe 10.

Plunger 30 with sealing means serves to hold the liquid contained in syringe barrel 20 and to variate the interior volume while maintaining a sealing of the interior during aspiration of the syringe and subsequently injection into a patient. As best seen in FIGS. 2 and 5, plunger 30 in its relaxed state resembles an inverted cup having:

a distal outside convex face 32 which is to interface with the liquid contained in syringe barrel 20;

a proximal inside face 34;

outside wall 36 contiguous with distal convex outside face 32;

inside wall 38 contiguous with proximal inside face 34; and bottom rim 39 which defines a circular opening in the cup-shaped plunger 30.

Outside wall 36 of plunger 30 comprises:

distal ring 40, proximal ring 41 and center ring 42, which are elastically deformable and extend radially outwardly from outside wall 36 and have, when taken together with plunger 30, a minimal diameter slightly in excess of the largest diameter of the working section of barrel 20. The rings form a sealing but slideable engagement with inside wall 21 of barrel 20.

Inside wall 38 of plunger 30 comprises: female threads 43 to receive and engage male threads 70 of plunger actuating cylinder 50. Prior to aspiration and injection of liquid into a patient, plunger actuating cylinder 50 is completely threaded into plunger 30 to mesh threads 43 with threads 70.

Referring to FIG. 6, plunger rod 80 is inserted into plunger actuating cylinder 50 so that flange 84 is located inside the plunger actuating cylinder, that is, just passed handle 62 of the plunger actuating cylinder. Knob 86 and flange 84 of plunger rod 80 serve as stopping means to limit the movement of plunger rod 80 in plunger actuating cylinder 50. Distance X is the distance allowed (which could be called protrusion distance) for movement of the plunger rod in the plunger actuating cylinder controlled by flange 84 and knob 86 which serve as stopping means. The longitudinal cross-section of the assembled syringe shown in FIG. 6 illustrates the various parts of the assembled syringe wherein:

X is the distance between flange 84 and knob 86;

Y is the total length of plunger 80, measured between plunger rod tip 82 and knob 86;

Z is the total length of the functional or working portion of syringe barrel 20; and W is the total length of plunger actuating cylinder 50 and plunger 30.

As shown in FIG. 6 and accentuated in FIG. 8, the plunger rod is in its base position, that is, plunger rod tip does not reach, and does not exert a force on, the inside face 34 of plunger 30. In this base position flange 84 contacts the handle 62 of plunger actuating cylinder 50.

Figure 9:
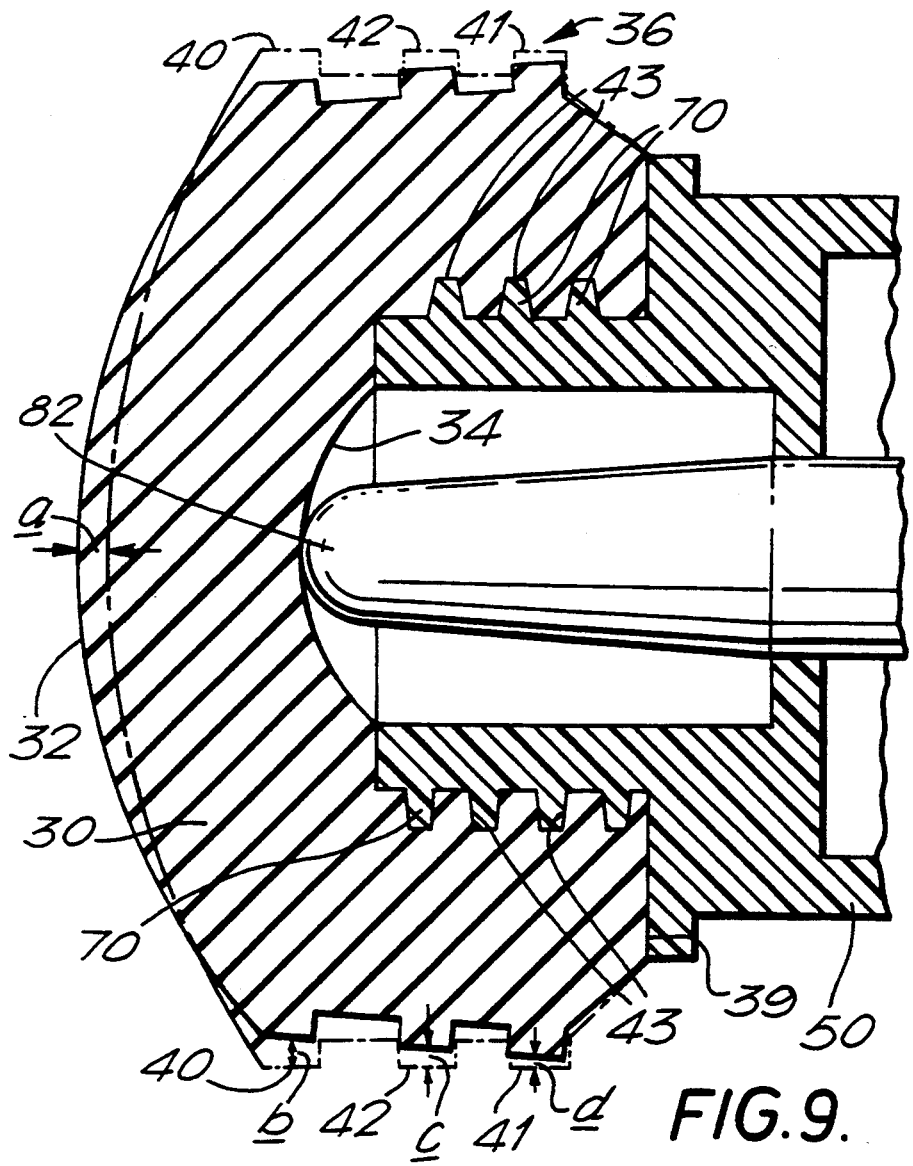
FIG. 9 is an enlarged fragmentary cross-section of the plunger, the plunger actuating cylinder and the plunger rod when the plunger rod is in its extended position.

In FIGS. 7 and 9 the syringe assembly 10 is depicted when plunger rod 80 is in its extended position: knob 86 is pushed against handle 62 and plunger rod tip 82 exerts force on inside face 34 of plunger 30. The force so exerted circumferentially deforms plunger 30: convex outside face 32 of plunger 30 is extended upward for distance "a", while distal ring 40, proximal ring 41 and center ring 42 are pulled inwardly by elastic tension forces for distances "b", "c" and "d" respectively. As illustrated, distance "a" is the largest, followed by distances "b", "c" and "d". This circumferential deformation of the plunger expels head gas from the syringe barrel, i.e. aspirates the syringe. Upon releasing the pressure applied on plunger rod 80, plunger 30 returns to its static position, thereby creating a vacuum in barrel 20 and drawing body fluid from the patient indicating that the desired site had been entered and the injection may commence. The operator then, again, exerts pressure on plunger rod 80 which results in the same circumferential deformation of plunger 30 as described with respect to aspirating the syringe. Referring to proximal ring 41, distal ring 40 and center ring 42, it is clear that the force they now exert on the inside wall 21 of barrel 20 is reduced in direct proportion to the distances "b", "c" and "d" created by the circumferential deformation. As a result, the plunger moves relatively easily in the barrel allowing convenient delivery of the liquid into the injection site. This advantage of the present invention is even more pronounced when the pre-filled syringe is kept in storage for extended time periods during which time the plunger tends to seize in the barrel and the interfacial force between the plunger and the inside wall of the barrel is extremely difficult to break in the axial direction. In the syringe of the present invention the force exerted on the plunger pulls the distal, proximal and center rings inwardly and greatly reduces the interfacial force between the plunger and the inside wall of the barrel.

Experiments were performed to find the most efficient lengths for X, Y, Z and W and their ratios for constructing syringe assemblies typically in use in pre-filled syringes. The following illustrates typical ranges measured in inches:

length of:
X: from 0.010 to 0.750
Y: from 2.000 to 6.000
Z: from 6.000 to 10.000 and
W: from 1.990 to 5.990

Their ratios are as follows:

$\frac{X}{Y}$ from 0.375 to 0.002

$\frac{X}{Z}$ from 0.125 to 0.001

$\frac{Y}{Z}$ from 1.000 to 0.200

$\frac{W}{X}$ from 2.650 to 599

$\frac{W}{Y}$ from 0.332 to 2.990

$\frac{W}{Z}$ from 0.199 to 0.998

The protrusion length of plunger rod 80, as defined by the ratio of X to Y, greatly influences the breakaway force of plunger 30 from inside wall 21 of syringe barrel 20. Using these ranges of lengths and length ratios in practicing the present invention, it will be appreciated that the syringe possess most of the attributes of an ideal syringe for both aspiration and injection as enumerated above. That is, the syringe is simple in construction, thus minimizing the cost of production; it is simple to operate; it is capable of manipulation with one hand; it is capable of multiple self-aspirating actions with each syringe or cartridge or; and it is capable of expelling air trapped within the syringe or cartridge either prior to initiation of the self-aspirating action or at any time during the sequence of actions necessary for injection of the syringe content without, on the one hand, precluding self-aspirating action at any point in the sequence or, on the other, rendering the self-aspirating action inoperative.

The operation of the pre-filled syringe of the present invention is as follows.

Plunger actuating cylinder 50, pre-assembled with plunger rod 80, is threaded into plunger 30 contained in the proximal end of syringe barrel 20 so that female threads 43 completely engage male threads 70. Plunger rod 80 at this point is in its base or static position within plunger actuating cylinder 50, that is, flange 84 is positioned against handle 62 of plunger actuating cylinder 50 and plunger rod tip 82 does not exert any pressure on inside face 34 of plunger 30. A hypodermic needle is snapped onto the tip 22 of syringe barrel 20. The practitioner then gains entry into the desired mammalian site, such as a blood vessel, using conventional venipuncture technique. The practitioner then exerts pressure on knob 86 of plunger rod 80 so that knob 86 is pushed against handle 62 of plunger actuating cylinder 50. In turn, tip 84 of plunger rod 80 will be forced against inside face 34 of plunger 30 resulting in a circumferential deformation of the plunger. Convex face 32 of plunger 30 is extended distally for distance "a", while distal ring 40, proximal ring 41 and center ring 42 are pulled inward by elastic tension for distance "b", "c" and "d" respectively. This circumferential deformation of the plunger expels head gas from the syringe, i.e. aspirates the syringe. At the same time the force exerted on the wall 21 of syringe barrel 20 by plunger 30 is greatly reduced facilitating the injection process after aspiration is completed. Upon releasing the pressure applied on plunger rod 80, plunger 30 returns to its original configuration thereby creating a vacuum in syringe barrel 20 and drawing body fluid from the patient indicating that the desired site had been entered and the injection may commence. If body fluid is not drawn, the injection site is to be changed and the aspiration process is to be repeated. At this point the practitioner is ready to inject the fluid into the site, and to that end, exerts pressure on the plunger rod 80 and plunger actuating cylinder 50. The pressure so exerted results in the same circumferential deformation of plunger 30 as described with respect to aspirating the syringe. Referring to proximal ring 41, distal ring 40 and center ring 42, it is clear that the force they now exert on the inside wall 21 of barrel 20 is reduced in direct proportion to the distance "b", "c" and "d" created by the circumferential deformation. As a result, the plunger moves relatively easily in the barrel allowing convenient delivery of the liquid into the injection site. This advantage of the present invention is even more pronounced when the pre-filled syringe is kept in storage for extended time periods during which time the plunger tends to seize in the barrel and the interfacial force between the plunger and the inside wall of the barrel is extremely difficult to break in the axial direction. In the syringe of the present invention the force exerted on the plunger pulls the distal, proximal and center rings inwardly and greatly reduces the interfacial force between the plunger and the inside wall of the barrel.

Having thus described the invention and the advantages thereof, it is considered that the invention is to be broadly construed and limited only by the following claims.

What is claimed is:

1. A syringe designed to be pre-filled and stored ready for injection comprising:
   (a) a barrel having an inner surface defining a cylindrical chamber for retaining an injectable fluid therein; said barrel having distal end terminating in a tapered tip to which an injection needle can be attached; and a proximal end for receiving a plunger;
   (b) a cup-shaped plunger slideably mounted in said barrel and positioned close to the proximal end of the barrel to provide a seal with the inner surface of the barrel, said plunger comprising:
      (1) a distal convex face which is to interface with the injectable fluid contained in the barrel;
      (2) a proximal face;
      (3) outside wall contiguous with the distal convex face having thereon: distal ring, proximal ring and center ring extending radially outwardly and forming a slideable seal with the inner surface of the barrel;
      (4) inside wall having female threads thereon; and
      (5) bottom rim which together with the inside wall defines a circular opening in the cup-shaped plunger through which a plunger actuating cylinder is inserted for engagement;
   (c) a plunger actuating cylinder having a distal end and a proximal end, for engaging the plunger comprising:
      (1) male threads at the distal end to engage female threads in the plunger; and
      (2) a handle at the proximal end; and
   (d) a plunger rod, having a distal end and a proximal end, fitted into said plunger actuating cylinder comprising:
      (1) a semi-circular shaped tip at the distal end with convex face projecting in the direction of the plunger and the diameter of which is substantially smaller than the diameter of the plunger to press against the proximal face of the plunger when pressure is being exerted on the plunger rod;
      (2) a knob at the proximal end located outside the plunger actuating cylinder and serving as first stopping means for the plunger rod to limit protrusion of the plunger rod into the proximal face of the plunger; and
      (3) a flange also at the proximal end but spaced from the knob and located within the plunger actuating cylinder and serving as second stopping means for the plunger rod to limit the movement of the plunger rod in the direction toward the proximal end of the plunger actuating cylinder;
      said first stopping means and second stopping means are designed to limit the movement of the plunger rod within the plunger actuating cylinder to a predetermined length defined by the distance between the first and second stopping means.

2. The syringe of claim 1 wherein said syringe barrel is made of an inert gas-impermeable material-selected from the group consisting of glass, polyethylene, polypropylene, polystyrenes, acrylic polymers and methacrylic polymers.

3. The syringe of claim 1 wherein said plunger is made of a compressible, elastomeric material.

4. The syringe of claim 1 wherein said plunger actuating cylinder and said plunger rod is made of a material selected from the group consisting of polyethylene, polypropylene, polystyrenes, acrylic polymers and methacrylic polymers.

5. The syringe of claim 1 wherein said plunger is circumferentially deformed in the direction of the distal end of the barrel upon exertion of a manual force on the plunger rod, thereby pulling said distal ring, proximal ring and center ring inwardly from the inner surface of the barrel and reducing the radial force exerted on the inner surface of the barrel.

6. The syringe of claim 5 wherein said distal ring, proximal ring, and center ring are pulled inward by elastic forces when pressure is exerted on said plunger rod.

7. A method of delivering a liquid medium into a patient from a pre-filled syringe, said syringe comprising:
   (a) a barrel having an inner surface defining a cylindrical chamber for retaining an injectable fluid therein; said barrel having distal end terminating in a tapered tip to which an injection needle can be attached; and a proximal end for receiving a plunger;
   (b) a cup-shaped plunger slideably mounted in said barrel and positioned close to the proximal end of the barrel to provide a seal with the inner surface of the barrel, said plunger comprising:
      (1) a distal convex face which is to interface with the injectable fluid contained in the barrel;
      (2) a proximal face;
      (3) outside wall contiguous with the distal convex face having thereon: distal ring, proximal ring and center ring extending radially outwardly and forming a slideable seal with the inner surface of the barrel;
      (4) inside wall having female threads thereon; and
      (5) bottom rim which together with the inside wall defines a circular opening in the cup-shaped plunger through which a plunger actuating cylinder is inserted for engagement;
   (c) a plunger actuating cylinder having a distal end and a proximal end, for engaging the plunger comprising:
      (1) male threads at the distal end to engage female threads in the plunger; and
      (2) a handle at the proximal end; and
   (d) a plunger rod, having a distal end and a proximal end, fitted into said plunger actuating cylinder comprising:
      (1) a semi-circular shaped tip at the distal end with convex face projecting in the direction of the plunger and the diameter of which is substantially smaller than the diameter of the plunger to press against the proximal face of the plunger when pressure is being exerted on the plunger rod;
      (2) a knob at the proximal end located outside the plunger actuating cylinder and serving as first stopping means for the plunger rod to limit protrusion of the plunger rod into the proximal face of the plunger; and
      (3) a flange also at the proximal end but spaced from the knob and located within the plunger actuating cylinder and serving as second stopping means for the plunger rod to limit the movement of the plunger rod in the direction toward the proximal end of the plunger actuating cylinder;

said first stopping means and second stopping means are designed to limit the movement of the plunger rod within the plunger actuating cylinder to a predetermined length defined by the distance between the first and second stopping means;

said method comprising the steps off
- (i) engaging a hypodermic needle with the tapered tip of said barrel;
- (ii) threading the plunger actuating cylinder into the plunger;
- (iii) gaining entry into the desired injection site on the patient;
- (iv) exerting a slight pressure on the plunger rod to expel head gas from the barrel;
- (v) releasing the pressure applied on the plunger rod to create vacuum in the syringe and drawing a small amount of body fluid from the patient and into the distal end of the barrel; and
- (vi) exerting pressure on the plunger actuating cylinder and plunger rod to move the plunger toward the distal end of the barrel thereby delivering the liquid medium into the patient.

8. The method of claim 7 wherein said syringe barrel is made of an inert gas-impermeable material selected from the group consisting of glass, polyethylene, polypropylene, polystyrenes, acrylic polymers and methacrylic polymers.

9. The method of claim 7 wherein said plunger is made of a compressible, elastomeric material.

10. The method of claim 7 wherein said said plunger actuating cylinder and said plunger rod is made of a material selected from the group consisting of polyethylene, polypropylene, polystyrenes, acrylic polymers and methacrylic polymers.

11. The method of claim 7 wherein said plunger is circumferentially deformed in the direction of the distal end of the barrel upon exertion of a manual force on the plunger rod, thereby pulling said distal ring, proximal ring and center ring inwardly from the inner surface of the barrel and reducing the radial force exerted on the inner surface of the barrel.

12. The method of claim 11 wherein said distal ring, proximal ring, and center ring are pulled inward by elastic forces when pressure is exerted on said plunger rod.

13. The method of claim 7 wherein said liquid medium is a pharmaceutical composition.

14. The method of claim 7 wherein said liquid medium is a diagnostic composition.

15. The method of claim 14 wherein said diagnostic composition is a contrast agent.

16. The method of claim 7 wherein said liquid medium is a biological agent.

* * * * *